United States Patent
Boettger et al.

(10) Patent No.: US 9,830,697 B2
(45) Date of Patent: Nov. 28, 2017

(54) DISPLAY OF DOSE VALUES FOR PLANNING AN IRRADIATION

(71) Applicants: Thomas Boettger, Heidelberg (DE); Mark Hastenteufel, Heidelberg (DE)

(72) Inventors: Thomas Boettger, Heidelberg (DE); Mark Hastenteufel, Heidelberg (DE)

(73) Assignee: Siemens Aktiengesellschaft, München (DE)

( * ) Notice: Subject to any disclaimer, the term of this patent is extended or adjusted under 35 U.S.C. 154(b) by 251 days.

(21) Appl. No.: 14/051,747

(22) Filed: Oct. 11, 2013

(65) Prior Publication Data
US 2014/0104275 A1 Apr. 17, 2014

(30) Foreign Application Priority Data
Oct. 11, 2012 (DE) .......................... 10 2012 218 529

(51) Int. Cl.
| | |
|---|---|
| *G06T 7/00* | (2017.01) |
| *A61N 5/10* | (2006.01) |
| *G06T 11/00* | (2006.01) |
| *A61B 6/00* | (2006.01) |

(52) U.S. Cl.
CPC .......... *G06T 7/0012* (2013.01); *A61N 5/1031* (2013.01); *G06T 11/001* (2013.01); *A61B 6/5217* (2013.01)

(58) Field of Classification Search
CPC .............................. A61B 6/032; A61B 6/5229
USPC ....................................................... 345/424
See application file for complete search history.

(56) References Cited

U.S. PATENT DOCUMENTS

| | | | | |
|---|---|---|---|---|
| 5,341,292 | A | * | 8/1994 | Zamenhof ............ A61N 5/1031 600/410 |
| 2007/0230761 | A1 | | 10/2007 | Gundel et al. |
| 2009/0175418 | A1 | * | 7/2009 | Sakurai et al. .............. 378/98.5 |
| 2012/0148131 | A1 | * | 6/2012 | Couch et al. ................. 382/131 |
| 2013/0303825 | A1 | * | 11/2013 | Bert ....................... A61N 5/103 600/1 |

FOREIGN PATENT DOCUMENTS

DE 102005059209 6/2007

OTHER PUBLICATIONS

Poon, E et al. "Brachygui: An Adjunct to an Accelerated Monte Carlo Photon Transport Code for Patient-Specific Brachytherapy Dose Calculations and Analysis". Journal of Physics: Conference Series 102 (2008): 012018.*
Afsharpour H. et al; "ALGEBRA: ALgorithm for the heterogeneous dosimetry based on GEANT4 for BRAchytherapy"; Phys. Med. Biol.; 2012; vol. 57; pp. 3273-3280.

(Continued)

*Primary Examiner* — Barry Drennan
*Assistant Examiner* — Shivang Patel
(74) *Attorney, Agent, or Firm* — Lempia Summerfield Katz LLC

(57) ABSTRACT

Dose values are displayed. The dose values display the take-up of radiation by an examination volume to be expected during an irradiation. An examination volume is segmented in an image, and the dose values are assigned to areas of the surface of the examination volume. The surface of the examination volume is displayed as a plane such that the areas displayed as flat will be graphically encoded by the dose values assigned to the respective areas.

19 Claims, 2 Drawing Sheets

(56) References Cited

OTHER PUBLICATIONS

Cho B. C. J. et al; "The development of target-eye-view maps for selection of coplanar or noncoplanar beams in conformal radiotherapy treatment planning"; Medical Physics; 1999; vol. 26; No. 11; pp. 2367-2372.
German Office Action cited in German Application No. 10 2012 218 529.1, dated May 23, 2013.
M. Hastenteufel et al.; "A Novel Method for Planning and Visualization of Ablation Lines for Atrial Fibrillation Treatment", Computing in Cardiology Conference,Sep. 19-22, 2004, Chicago, Illinois, USA, pp. 13-16.
Poon E. et al; "BrachyGUI: an adunct to an accelerated Monte Carlo photon transport code for patient-specific brachytherapy dose calculations and analysis"; Journal of Physics: Conference Series 102; 2008; No. 012018;pp. 1-8.
Rieder et al.: "Visual Support for Interactive Post-Interventional Assessment of Radiofrequency Ablation Therapy", in Eurographics / IEEE-VGTC Symposium on Visualization, vol. 29, 2010, No. 3,pp. 1093-1102.
Troost E. G. C. et al; "Innovations in Radiotherapy Planning of Head and Neck Cancers: Role of PET"; Journal of Nuclear Medicine; 2010; vol. 51; No. 1; pp. 66-76.

\* cited by examiner

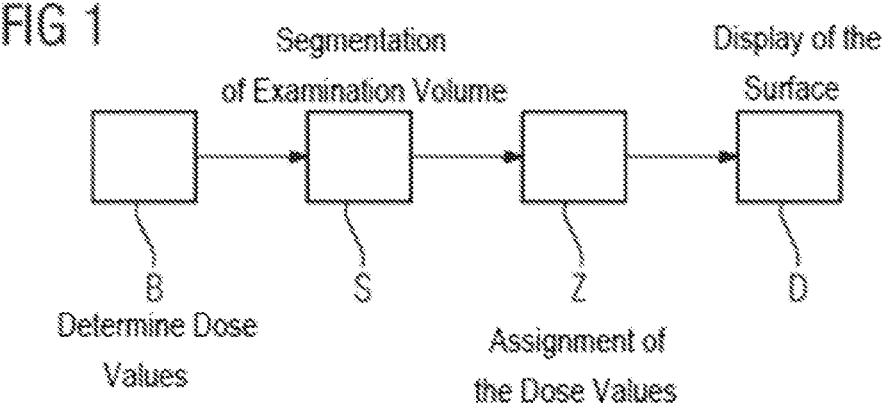
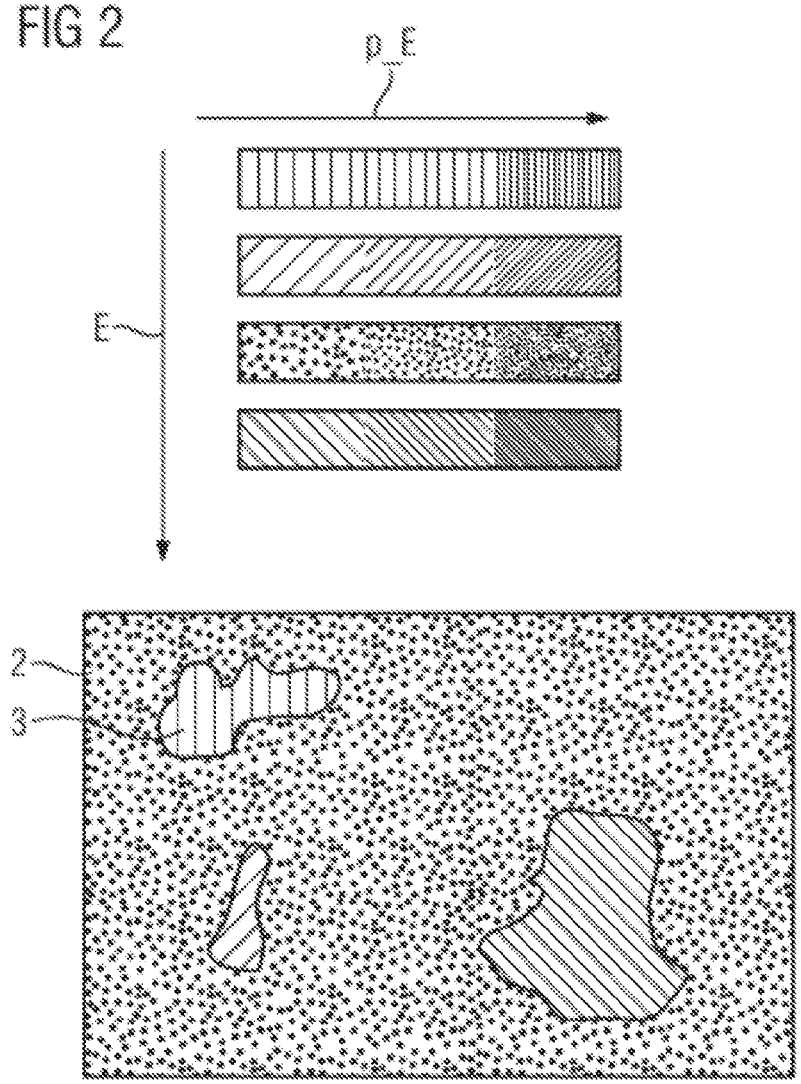

DISPLAY OF DOSE VALUES FOR PLANNING AN IRRADIATION

This application claims the benefit of DE 10 2012 218 529.1, filed on Oct. 11, 2012, which is hereby incorporated by reference in its entirety.

BACKGROUND

The present embodiments relate to a method and a device for display of dose values for planning an irradiation.

X-rays and particle rays are used for the treatment of tumors. Such treatment requires an irradiation plan that defines the time at which and the intensity with which the radiation is applied. To create an irradiation plan, the position and also the form of the examination volume (e.g., the tumor) is to be determined. Such a determination may be undertaken with an imaging method such as computed tomography (CT) or magnetic resonance tomography (MRT).

An objective of the irradiation plan is to optimize the irradiation with respect to dose distribution. In the treatment of tumors, the desire is for as much as possible of the dose to be taken up by the tumor and as little as possible of the dose to be taken up by surrounding, healthy tissue. Irradiation methods may also be used in non-therapeutic areas (e.g., in the irradiation of phantoms or non-living bodies as part of research work, or in the irradiation of materials). In such cases, an optimization of the dose distribution is desirable.

The dose values determined before the actual irradiation are displayed graphically, so that the irradiation plan may be assessed. The form in which the dose values are displayed may be such that the dose values are able to be assessed as quickly and as reliably as possible. The important information about the distribution of the dose is to be displayed, and the display is simplified far enough for the significant aspects of the dose distribution to be detected quickly and reliably.

The publication by Rieder et al., "Visual Support for Interactive Post-Interventional Assessment of Radiofrequency Ablation Therapy," Eurographics/IEEE-VGTC Symposium on Visualization, Volume 29, Number 3 (2010), discloses a method for visualizing the map of a tumor for reliable assessment of an ablation therapy. In ablation therapy for treating liver tumors, electrical energy is created locally by electrodes, so that tumor cells are destroyed locally by the resistive heat arising. To be able to plan the ablation therapy and assess the success of the treatment, CT images of the tumor are recorded before and after the therapeutic intervention. This method includes, based on the CT images, the color coding of the ablation state of the tumor in accordance with the traffic light colors green, orange and red. The 2D slice images of the tumor are color-coded and are used for an additional intuitive visualization. Then the color coding is mapped onto the surface of a rendered 3D volume of the tumor. The surface of the tumor is also represented in the form of a 2D map. This may be achieved by spherical parameterization as well as by the subsequent smoothing of the surface.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the dose values determined as part of an irradiation plan are displayed so that the irradiation plan may be assessed quickly and safely on the basis of the dose values displayed.

The features, advantages or alternate embodiments mentioned here are likewise to be transferred to the other subject matter and vice versa. In other words, the objectives, which are directed to an arrangement, for example, may also be further developed with the features that are described in connection with a method. The corresponding functional features of the method are embodied in such cases by corresponding objective modules.

Dose values are displayed. The dose values are a measure of the expected take-up of radiation by an examination volume during radiation therapy. One or more of the present embodiments include the segmentation of an examination volume in an image as well as the assignment of the dose values to areas of the surface of the examination volume. The surface of the examination volume is displayed as a plane such that the areas displayed as flat are graphically encoded by the dose values assigned to the respective areas. This is because a display of the surface of the examination volume as flat enables the information encoded in or together with the surface to be detected more rapidly. The fact that the dose values assigned to the individual areas of the surface are graphically encoded enables information about the distribution of the dose values in the tumor volume to be detected at a glance and thus assessed rapidly. The intuitive display of the dose values in one plane avoids misinterpretations, so that the method also makes possible a safe assessment of the distribution of the dose values and thus of the underlying irradiation plan.

In a further embodiment, the values are assigned by a projection of dose values, starting from a point in the segmented examination volume, through which the dose values within the examination volume may be assigned in an easily-verifiable manner to the surface of the examination volume.

If the dose values include pairs of absolute dose values as well as probability values linked to the respective absolute dose values, then the safety of the assessment of the irradiation plan is increased based on the display of the dose values. This is because the probability values specify how probable it is that an absolute dose value will actually also be realized in the future irradiation.

If the display includes the areas being encoded by the assigned dose values in the form of a color value and/or a brightness value, then the information for distributing the dose values may be detected especially intuitively and rapidly.

In a further embodiment, the display includes areas of the surface, the assigned dose values of which exceed a threshold, being graphically encoded in a uniform manner in accordance with the threshold. This simplifies the display, so that the information about the distribution of the dose values may be detected intuitively and quickly.

In a further embodiment, the dose values are assigned to different points in time of the irradiation to be planned. The display includes the display of a number of surfaces for the different points in time in the form of a number of planes. This enables the take-up of the dose during the irradiation over the course of time to be displayed, which makes it easier to identify errors in the irradiation plan.

A further embodiment includes the definition of the dose values so that a direct display and subsequent assessment of the dose values is made possible.

If the determination and also the display are carried out such that a spatial displacement and/or deformation of the examination volume are taken into account during the irradiation, the safety in the assessment of the dose distribution is increased even further.

In one embodiment, an apparatus for display of dose values is provided. The dose values display the take-up of radiation by an examination volume to be expected during an irradiation. The apparatus includes an image processing unit configured for segmentation of an examination volume in an image, for assignment of the dose values to areas of the surface of the examination volume and also for display of the surface of the examination volume as a plane such that the areas displayed as flat are graphically encoded by the dose values assigned to the respective areas.

The apparatus is also configured for carrying out one of the aforementioned methods with the corresponding advantages quickly, repeatedly and robustly.

If the apparatus is also configured to irradiate an examination volume, the irradiation plan assessed by the method of one or more of the present embodiments may be applied directly.

In a further embodiment, the apparatus is configured to record a spatial three-dimensional image of the examination volume.

In one embodiment, a computer program with program code for carrying out the method acts in accordance with one of the methods when the computer program is executed in a computer is provided. This enables the method to be carried out in a rapid, repeatable and robust manner.

BRIEF DESCRIPTION OF THE DRAWINGS

FIG. 1 shows a flow diagram of one embodiment of a method;
FIG. 2 shows an exemplary display of dose values.

DETAILED DESCRIPTION

Figure 3:
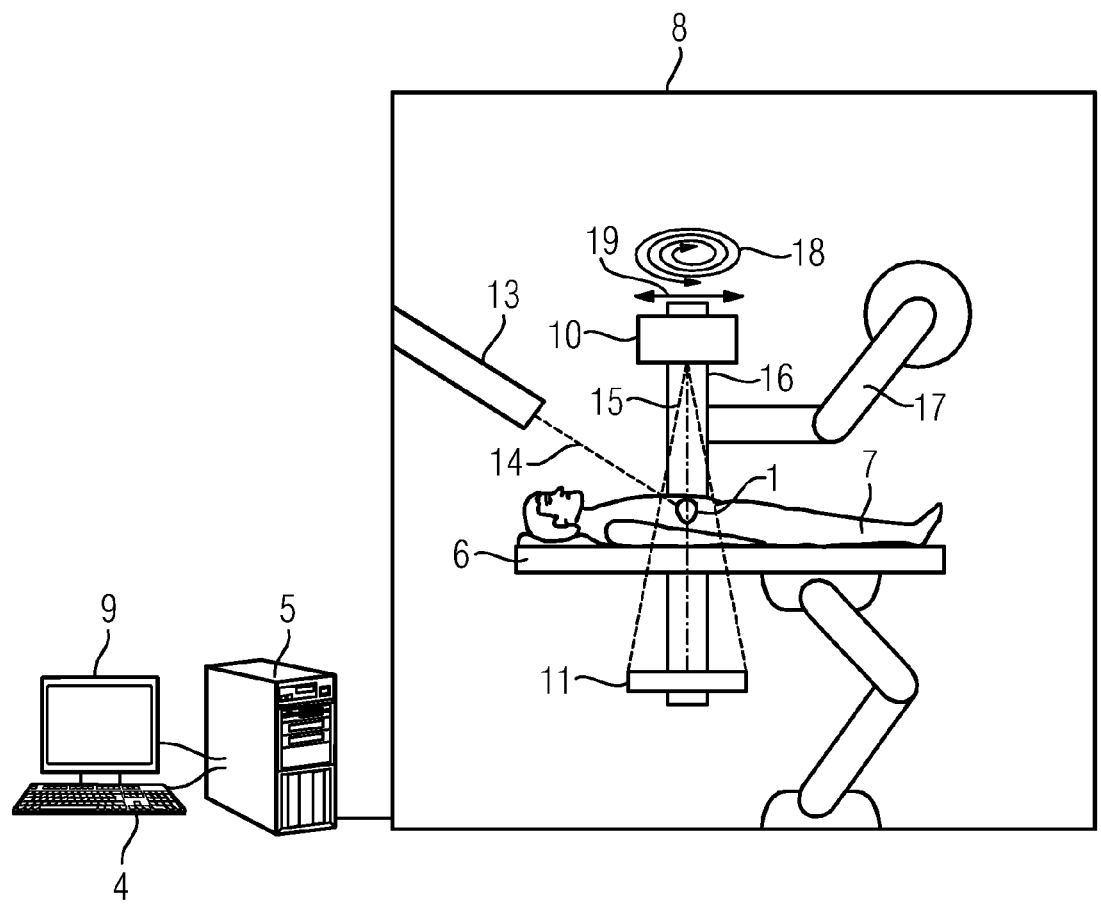
FIG. 3 shows one embodiment of an apparatus for displaying dose values.

FIG. 1 shows a flow diagram of one embodiment of a method for display D of dose values. The dose values are a measure of a take-up of radiation by an examination volume 1 to be expected during an irradiation. In such an irradiation, an irradiation unit moves around a fixed-position patient 7 and emits radiation, for example, in the form of x-rays 15 as precisely as possible onto the examination volume 1. The display of dose values is a usual step in the planning of an irradiation (e.g., for treatment of cancer). The dose values to be expected are determined within the framework of a radiation plan based on a mathematical model as well as with reference to the known form of the examination volume 1. This uses the recording of an image of the examination volume 1. The object of the irradiation plan is to regularly optimize the irradiation such that as much of the dose as possible is taken up by the examination volume 1 (e.g., by a tumor), and as little as possible of the dose is taken up by the surrounding area.

The dose in such cases is understood, for example, to be the energy dose (e.g., the energy of the radiation that a patient 7 absorbs per kg of body weight). The Gray unit is used for a dose defined in such terms. The dose may also be understood as the effective dose in Sievert units. A dose value involves at least one absolute dose value that specifies a numerical value for a dose (e.g., in Gray or Sievert units). Radiation within the meaning of the application involves the controlled and directed emission of particles such as electrons or ions or of electromagnetic radiation such as x-rays 15 using an irradiation unit. The irradiation unit involves a beam exit 13 for a particle beam 14 or an x-ray emitter 10.

The method includes the segmentation S of an examination volume 1 in an image. The segmentation S of the examination volume 1 automatically defines the surface of the volume. This makes a direct assignment Z of the previously defined dose values to areas 3 of the surface of the examination volume 1 possible. A display D of the surface of the examination volume 1 as a plane 2 is undertaken such that the areas 3 displayed as flat are graphically encoded by the dose values assigned to the respective areas 3. In other words, the display D involves a flat map of the surface of the examination volume 1. The dose values contribute to the mapping in the form of a graphical encoding.

An image may involve a digital image that is recorded by an imaging device such as an MRT or CT device. For example, such an image may involve a medical image (e.g., an image that is recorded for medical purposes such as the diagnosis or the planning of a therapeutic irradiation). Images may involve further processing (e.g., filtered images). An image may be of both a spatial two-dimensional nature and may be constructed from pixels and also of a spatial three-dimensional nature and may be constructed from voxels.

The image in which the examination volume 1 is segmented involves a spatial three-dimensional data set. A medical image may be recorded by high-resolution imaging modalities such as MRT or CT. This is because these techniques offer a high spatial resolution and thus make possible a precise determination B of the dose values for the examination volume 1 as well as for the surrounding tissue. Contrast media may be used to facilitate the segmentation S of the examination volume 1 in the medical image. This is because certain contrast media collect in tumors and thus help to delimit the tumors from the surrounding tissue. Such media that improve the imaging of structures and functions of the body are defined as contrast media. For example, contrast media containing iodine are in widespread use. A contrast medium may also involve a tracer, an artificial, often radioactively-marked substance from the body or from outside the body, which, after introduction into the living body, participates in the metabolism and in addition makes possible or facilitates a very wide variety of examinations.

After an image of the examination volume 1 is recorded, the determination B of the dose values is undertaken. The determination B is undertaken such that each volume element of the examination volume 1 is assigned a dose value. This, for example, involves the energy that will be absorbed by the respective volume elements during the planned irradiation. The determination B of the dose values may be undertaken in a time-resolved manner. This provides that a dose value assigned to a specific volume element may include a number of absolute dose values E that in each case include the energy absorbed by the volume element in a certain period of time during the irradiation. The determination B may be undertaken such that the absolute dose values E are each assigned a probability value p_E that specifies the probability that the respective absolute dose value E will actually be absorbed during the planned irradiation. The determination B of the probability values p_E takes account of the following error factors, for example: movement of the patient 7 and thus of the examination volume 1 during the planned irradiation; accuracy of the segmentation S; accuracy of the positioning of the patient 7; and accuracy of the data of the image of the examination volume 1 (e.g., in the form of Hounsfield values).

One option for determining the probability values is a multiple determination of the absolute dose values E with different parameters of an error factor. Thus, an absolute dose value E may be calculated multiple times with varied Hounsfield values. The resulting standard deviation is then a possible probability value p_E.

The segmentation S is undertaken, for example, by a threshold value method or by a region-oriented method such as Region Growing or Region Splitting or with the aid of edge extraction. The examination volume 1 involves a contiguous volume that is surrounded by a closed surface. For example, many tumors may be described in a simplified manner as spheres or ellipsoids, so that a segmentation S may be undertaken effectively and quickly.

Since each volume element of the examination volume 1 is already assigned a dose value through the determination B, the examination volume 1 may already be shown as a display in which the individual volume elements are graphically encoded in accordance with corresponding assigned dose values. For example, the examination volume 1 may be displayed in the form of parallel slice images. In each slice, image flat areas that correspond to a volume element encode the dose values in color. A brightness encoding of the dose values is possible in order, for example, to display the probabilities associated with the respective absolute dose values E.

The method also includes, in one embodiment, the reconstruction of the surface of the segmented examination volume 1. Such a reconstruction is undertaken, for example, by "Volume Rendering (VR) or by "Maximum Intensity Projection" (MIP). A surface reconstructed this way is displayed by the Surface Shaded Display technique, for example.

There is an assignment Z of the dose values to individual areas 3 of the surface. The areas 3 involve surface elements of comparable size in order to obtain, as homogeneous as possible, a resolution of the dose values on the surface. The shape and size of the surface elements may be produced from the assignment specification of the assignment Z by, for example, all dose values, starting from a point in the examination volume 1, being projected within an angular range onto the surface. This angular range may, for example, be embodied as spherical or in the shape of the pyramid. The point, for example, involves the geometrical focal point of the examination volume 1 that is produced from a homogenous mass distribution of the segmented examination volume 1. In such cases, both the maximum and also the minimum or the average value of the volume projected within a specific angular range may be assigned to the corresponding area 3 of the surface. The angular range then defines the shape and size of the surface elements.

There may be a display D of the surface of the examination volume 1 located in the three-dimensional space together with the assigned dose values. In such a display D, the dose values assigned to the individual areas 3 are graphically encoded, such as in color corresponding to a color scale. A brightness encoding of the dose values may be provided in order, for example, to display the probability values p_E associated with the respective absolute dose values E.

FIG. 2 shows a display of dose values in accordance with one embodiment of a method. The display D of the surface of the examination volume 1 as plane 2 uses a specification, in accordance with which the three-dimensional coordinates of the individual areas 3 of the surface are transferred into the two-dimensional coordinates of a plane 2. Such transfers are also known as map projections. Such a transfer may occur by the surface being spherically parameterized and subsequently smoothed. Examples of map projections are the spherical projections and the cylindrical mappings such as the Mercator projection or the Mollweide projection.

If the dose values include pairs of absolute dose values E as well as the probability values p_E associated with the respective absolute dose values E, then the absolute dose values E as well as the probability values p_E may be graphically encoded differently in the display D. For example, the absolute dose values E may be encoded in accordance with a color scale, and the probability values p_E may be encoded in accordance with a brightness scale.

The graphical encoding of the absolute dose values E in accordance with a color scale may be undertaken continuously. As an alternative to this, areas 3 of the surface, for which the assigned dose values are below a threshold, may be graphically encoded uniformly in accordance with the threshold. This provides that, for example, areas 3 to which absolute dose values E that are above a first threshold are assigned are shown in orange, and all areas 3 to which absolute dose values E that exceed a second, higher threshold are assigned are shown in red. This produces isolines of the absolute dose values E that facilitate an interpretation of the distribution of the absolute dose values E. This is because the display D using isolines makes it easier to identify "cold spots" or "hot spots" (e.g., regions of the examination volume 1 that absorb especially little or especially much radiation in accordance with the irradiation plan). The display D of an area 3 of the surface in accordance with a threshold may, however, also be based on a value other than the absolute dose value E (e.g., on the standard deviation of the absolute dose values E in the volume projected on the area 3).

If the dose values are also assigned to different points in time of the irradiation, then the display D includes a display of a number of surfaces for the different points in time in the form of a number of planes 2. The number of planes 2 may be displayed behind one another, so that a film that displays the development of the take-up of the radiation by the examination volume 1 over time is produced. Such a display D is helpful in revealing the reason for "cold spots" or "hot spots" being produced. For example, the proportion of radiation below a certain angle of the irradiation unit at a certain point in time may be so great that a "hot spot" is produced by the proportion of radiation.

The dose values may not only be assigned to points in time but also time intervals associated therewith, in which the respective points in time lie. In an option for displaying a number of surfaces for the different points in time, a plane carries the information about the dose that is taken up in the time interval assigned. In a further option for displaying a number of surfaces for the different points in time, a plane carries the information about the dose that is taken up cumulatively up to the time interval assigned to.

A spatial displacement may be simulated before or during the irradiation in order to be able to estimate consequences. If the determination B includes the determination of dose values for a defined spatial displacement and/or deformation of the examination volume 1 during the irradiation, then the display D may also take into account such a displacement and/or deformation. Such a displacement and/or deformation may either be considered as a sum, in that only the dose values at the end of the irradiation are displayed D, or the displacement and/or deformation may be taken into consideration resolved over time, in that a film of the planes 2 is shown, during which the examination volume 1 is displaced or deforms.

FIG. 3 shows one embodiment of an apparatus for displaying dose values. The patient 7 is supported for the recording of an image and also for the subsequent irradiation on a patient couch 6. The height and orientation of the patient couch 6 may be adjusted. An image of the examination volume 1 for dose calculation is recorded mostly on a separate, high-resolution MRT or CT device, which is not shown here. An image of the examination volume 1 may be recorded directly before the irradiation in order to correctly position the patient 7. To record an image in the form of a tomographic x-ray image, the x-ray emitter 10 and the x-ray detector 11 are rotated around the longitudinal axis of the patient 7. The x-ray emitter 10 may involve an x-ray tube. The x-ray detector 11 may involve a row or flat panel detector, but the x-ray detector 11 may also be embodied as a scintillator counter or CCD camera. Such a rotation may be provided through the robot arm 17, on which the x-ray emitter 10 and the x-ray detector 11 are connected by a common carrier arm 16. The carrier arm 16, in the embodiment shown, involves a C-arm.

The x-ray emitter 10, the x-ray detector 11, the carrier arm 16 and the robot arm 17 form an irradiation unit. This is because the actual irradiation may be undertaken by x-rays 15. During the irradiation, the x-ray emitter 10 and the x-ray detector 11 are moved together around the examination volume 1 of the patient 7. For example, the x-ray emitter 10 and the x-ray detector 11 may move along the path of a spiral 18 or perform a regular pivoting movement within the pivot area 19.

The irradiation unit may, however, also include a beam exit 13 as well as the unit (not shown here) for generating and accelerating particles. Irradiation by a particle beam 14 uses a beam exit 13. Before reaching the beam exit 13, the particles such as electrons or ions, for example, have been generated and accelerated. The beam exit 13 may, as shown, be located in a screened room 8 and separate from the unit for generating and accelerating particles. The radiation unit for creation and emission of particle beams may, however, also, like the irradiation unit for generation and emission of x-rays 15, be embodied as a compact unit and be located completely in the room 8.

In the example shown, the computer 5 for controlling the beam exit 13 as well as the x-ray units and further units such as the height-adjustable patient couch 6 are set up outside the shielded room 8. The computer may, however, also be located inside the room 8. The computer 5 may also include the image processing unit that is configured to carry out the method of one or more of the present embodiments, as previously described. The image processing unit may be embodied both in the form of hardware (e.g., a processor) and also of software. Thus, a part of the image processing unit may be embodied as a field programmable gate array (FPGA) or may include an arithmetic logic unit. For example, the image processing unit may be realized on different computers 5. The computer 5 is connected to an input unit 4 and also to an output unit 9, which may be used for displaying D the surface of the examination volume 1. The output unit 9 may, for example, involve one or more LCD, plasma or OLED screen(s). The output on the output unit 9 involves, for example, a graphical user interface for manual input of patient data as well as a recording mode. The input unit 4 involves a keyboard, a mouse, a touchscreen or also a microphone for voice input, for example.

The use of input unit 4 and output unit 9 allows switching between different displays of the surface of the examination volume 1 in order to modify these. For example, the observer may first select a three-dimensional display of the rendered surface of the examination volume 1 in order to switch to a display D of the surface in the form of a plane 2. The observer may then select different thresholds for absolute dose values and select the color scale for colored encoding of the different dose values within the threshold ranges. In a display D of a time curve of the take-up of the dose during the irradiation, the time intervals (e.g., in images per second) may be selected.

In one embodiment, a computer program with program code is stored in a non-transitory computer-readable storage medium for carrying out the previously described method when the computer program is executed in a computer 5. The computer program is configured so that the computer program may execute specific method acts using the computer 5 (e.g., one or more processors). The computer 5 includes, for example, a corresponding main memory, a corresponding graphics card or corresponding logic unit, so that the respective method acts may be efficiently executed. The computer program may also be embodied as a part of the apparatus for displaying dose values.

Although the invention has been illustrated and described in greater detail on the basis of the exemplary embodiments, the invention is not limited by the disclosed examples, and other variations may be derived herefrom by the person skilled in the art without departing from the scope of protection of the invention. For example, method acts may be carried out in a sequence other than that specified.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for displaying dose values, wherein the dose values are a measure for a take-up of radiation by an examination volume to be expected during an irradiation, the method comprising:
   segmenting, by an image processor, the examination volume into an image;
   assigning the dose values to areas of a surface of the examination volume; and
   displaying, by a display in communication with the image processor, the surface of the examination volume as a plane such that areas displayed as flat are graphically encoded by the dose values assigned to the respective areas,
   wherein the dose values comprise pairs of absolute dose values and probability values associated with the respective absolute dose values, and
   wherein displaying the surface of the examination volume comprises displaying a representation of the absolute dose values and a representation of the probability values together on the surface of the examination volume, the absolute dose values being displayed according to a first type of graphical encoding and the probability values being displayed according to a second type of graphical encoding, such that voxels represented within the plane are graphically encoded in accordance with the corresponding absolute dose values and probability values via the first type of graphical encoding and the second type of graphical encoding, respectively.

2. The method of claim 1, wherein the assigning comprises projecting the dose values, starting from a point in the segmented examination volume.

3. The method of claim 1, wherein the displaying comprises encoding the areas by the assigned dose values in the form of a color value, a brightness value, or the color value and the brightness value.

4. The method of claim 3, wherein the absolute dose values are encoded in the form of a color value and the probability values are encoded in the form of a brightness value.

5. The method of claim 1, wherein the displaying comprises encoding areas of the surface for which the assigned dose values exceed a threshold graphically in a uniform manner in accordance with the threshold.

6. The method of claim 1, further comprising assigning the dose values to different points in time of the irradiation, wherein the displaying comprises displaying a plurality of surfaces at the different points in time in the form of a plurality of planes.

7. The method of claim 1, further comprising determining the dose values.

8. The method of claim 7, wherein the determining and the displaying take account of a defined spatial displacement, deformation of the examination volume during the irradiation, or a combination thereof.

9. An apparatus for displaying dose values, wherein the dose values display a take-up of radiation by an examination volume to be expected during an irradiation, the apparatus comprising:
an image processor configured to:
segment an examination volume in an image;
assign the dose values to areas of a surface of the examination volume; and
display the surface of the examination volume as a plane such that the areas displayed as flat are graphically encoded by the dose values assigned to the respective areas,
wherein the dose values comprise pairs of absolute dose values and probability values associated with the respective absolute dose values, and
wherein the display of the surface of the examination volume comprises display of a representation of the absolute dose values and a representation of the probability values together on the surface of the examination volume, the absolute dose values being displayed according to a first type of graphical encoding and the probability values being displayed according to a second type of graphical encoding, such that voxels represented within the plane are graphically encoded via the first type of graphical encoding and the second type of graphical encoding in accordance with the corresponding respective absolute dose values and probability values, respectively.

10. The apparatus of claim 9, further comprising an irradiation device configured to irradiate the examination volume.

11. The apparatus of claim 9, wherein the image processing unit is configured to record a spatial three-dimensional image of the examination volume.

12. A non-transitory computer-readable storage medium that stores a computer program with program code having instructions executable by a computer to display dose values, wherein the dose values are a measure for a take-up of radiation by an examination volume to be expected during an irradiation, the instructions comprising:
segmenting the examination volume into an image;
assigning the dose values to areas of a surface of the examination volume; and
displaying the surface of the examination volume as a plane such that areas displayed as flat are graphically encoded by the dose values assigned to the respective areas,
wherein the dose values comprise pairs of absolute dose values and probability values associated with the respective absolute dose values, and
wherein displaying the surface of the examination volume comprises displaying a representation of the absolute dose values and a representation of the probability values together on the surface of the examination volume, the absolute dose values being displayed according to a first type of graphical encoding and the probability values being displayed according to a second type of graphical encoding, such that voxels represented within the plane are graphically encoded via the first type of graphical encoding and the second type of graphical encoding in accordance with the corresponding respective absolute dose values and probability values, respectively.

13. The non-transitory computer-readable storage medium of claim 12, wherein the assigning comprises projecting the dose values, starting from a point in the segmented examination volume.

14. The non-transitory computer-readable storage medium of claim 12, wherein the displaying comprises encoding the areas by the assigned dose values in the form of a color value, a brightness value, or the color value and the brightness value.

15. The non-transitory computer-readable storage medium of claim 14, wherein the absolute dose values are encoded in the form of a color value and the probability values are encoded in the form of a brightness value.

16. The non-transitory computer-readable storage medium of claim 12, wherein the displaying comprises encoding areas of the surface for which the assigned dose values exceed a threshold graphically in a uniform manner in accordance with the threshold.

17. The non-transitory computer-readable storage medium of claim 12, wherein the instructions further comprise assigning the dose values to different points in time of the irradiation, wherein the displaying comprises displaying a plurality of surfaces at the different points in time in the form of a plurality of planes.

18. The non-transitory computer-readable storage medium of claim 12, wherein the instructions further comprise determining the dose values.

19. The non-transitory computer-readable storage medium of claim 18, wherein the determining and the displaying take account of a defined spatial displacement, deformation of the examination volume during the irradiation, or a combination thereof.

* * * * *